United States Patent
Bergman et al.

(10) Patent No.: US 10,130,101 B2
(45) Date of Patent: *Nov. 20, 2018

(54) SABADILLA OIL

(71) Applicant: McLaughlin Gormley King Company, Golden Valley, MN (US)

(72) Inventors: John Thomas Bergman, Saint Louis Park, MN (US); Darrick David Unger, Minnetonka, MN (US); Robert A. Suranyi, Minneapolis, MN (US)

(73) Assignee: MCLAUGHLIN GORMLEY KING COMPANY, Golden Valley, MN (US)

( * ) Notice: Subject to any disclaimer, the term of this patent is extended or adjusted under 35 U.S.C. 154(b) by 286 days.

This patent is subject to a terminal disclaimer.

(21) Appl. No.: 15/299,826

(22) Filed: Oct. 21, 2016

(65) Prior Publication Data

US 2017/0112139 A1  Apr. 27, 2017

Related U.S. Application Data

(60) Provisional application No. 62/244,889, filed on Oct. 22, 2015.

(51) Int. Cl.
| *A61K 36/00* | (2006.01) |
| *A01N 65/40* | (2009.01) |
| *A01N 25/04* | (2006.01) |
| *A01N 65/42* | (2009.01) |

(52) U.S. Cl.
CPC .............. *A01N 65/40* (2013.01); *A01N 25/04* (2013.01); *A01N 65/42* (2013.01); *Y02A 50/324* (2018.01)

(58) Field of Classification Search
CPC ....................................................... A61K 36/00
USPC ......................................................... 424/725
See application file for complete search history.

(56) References Cited

U.S. PATENT DOCUMENTS

| 2,348,949 A | 5/1944 | Allen et al. |
| 2,390,911 A | 12/1945 | Allen et al. |
| 2,726,188 A | 12/1955 | Allison et al. |
| 3,078,211 A | 2/1963 | Allison et al. |
| 3,169,903 A | 2/1965 | Stoutamire et al. |
| 6,309,678 B1 | 10/2001 | Kahol et al. |

OTHER PUBLICATIONS

International Search Report and Written Opinion issued by the International Bureau in corresponding application No. PCT/US2016/058061 dated Jan. 17, 2017.

*Primary Examiner* — Michael V Meller
(74) *Attorney, Agent, or Firm* — Wood, Phillips, Katz, Clark & Mortimer

(57) ABSTRACT

The invention relates to methods for controlling pests by application of sabadilla oil to pests' environment or to pests. This present invention is also directed to methods for producing sabadilla oil by removing the oil from plants.

1 Claim, No Drawings

SABADILLA OIL

FIELD OF THE INVENTION

The present invention is directed to the use of sabadilla oil as a pesticide and to methods of producing sabadilla oil.

BACKGROUND OF THE INVENTION

Controlling damaging pests on plants grown to provide human food is a constant struggle for growers. Insects can completely destroy a harvest and can cause catastrophic food shortages or financial ruin for the growers. Although many products are effective against insects and mites that damage plants, the products must also be safe enough to be released into the growing environment and safe enough to be applied to parts of the plants that will eventually be consumed.

Organic farming is increasing in popularity. Organic farming restricts the use of compounds that are used for pest control to encourage sustainability and safety. Insecticides can be used in organic farming if they are considered "natural." Unfortunately, many of the natural insecticides currently available are not potent enough to provide adequate insect control. Further, many of the currently available natural insecticides are not practical to apply or their application is cost prohibitive.

One effective naturally derived insecticide is found in the tissues of many of the plants of the genus *Schoenocaulon*. The species with the longest history of use, and the most readily available, is the Sabadilla Lily (*Schoenocaulon officinale*). The plant is indigenous to Central and South America and its seeds have been used for centuries for their insecticidal properties. The seeds contain the alkaloids veratridine and cevadine, both of which are known to be active against arthropods.

Usually the dried seeds are ground to a powder and the powder is applied dry or wetted to the insects. The dust from the seeds, however, can cause eye and nasal irritation. Another disadvantage of using the ground seeds is that the alkaloids break down quickly in the sunlight and do not provide any residual protection.

U.S. Pat. Nos. 2,348,949 and 2,390,911 disclose the use of ground sabadilla seeds with beta-butoxy-beta-prime-thiocyanodiethyl-ether to control house flies. Further, these patents teach heating the seeds and using them as a powder, or mixing them with kerosene to form a sprayable formulation. Neither of these disclosed mixtures of ground sabadilla seeds would be appropriate for organic farming.

Further, insect infestation of human living spaces is a persistent problem. Bed bugs (*Cimex lectualrius*) are known vectors of human disease and are difficult to detect because they are small and often emerge from their hiding spots at night. Currently, there are limited means of capturing and containing bed bugs. Often, an insecticide is the only way to thoroughly treat an environment. Unfortunately, current insecticides are inadequate to provide the mortality rates necessary to completely eliminate an infestation. Another issue that has emerged is that some colonies have developed very high resistance to pyrethroid treatments. The Environmental Protection Agency ("EPA") has determined that pyrethroid-resistant colonies pose a significant human health risk.

Accordingly, there is a need for new methods of controlling pests on plants and in human living spaces. The methods should be potent, safe to apply, and safe for the environment.

SUMMARY OF THE INVENTION

In one aspect, the present invention is directed to methods for controlling pests comprising applying sabadilla oil to pests or to their environment.

In another aspect, the present invention is directed to methods for extracting sabadilla oil from plants of the *Schoenocaulon* genus.

In yet another aspect, the present invention is directed to a pesticidal sabadilla oil product produced by the process comprising the steps of milling sabadilla seeds, washing the milled sabadilla seeds with at least one extract solvent selected from the group consisting of C5 to C14 alkanes, chlorinated methane, chlorinated ethane, benzene, and benzene derivatives under agitation to produce a sabadilla oil solution, removing the solution from the washed milled seeds, and removing the extract solvent from the solution to produce the sabadilla oil.

In a further aspect, the present invention is directed to a pesticidal sabadilla product produced by the process comprising the steps of milling sabadilla seeds, washing the milled sabadilla seeds with at least one seed or plant part solvent selected from the group consisting of methanol, ethanol, glycol ether, ethyl lactate, propanol, butyl lactate, gamma-butyrolactone, and 1-butanol to produce a sabadilla oil solution, removing the solution from the washed milled seeds, removing the seed or plant part solvent from the solution to produce a sabadilla oil, washing the sabadilla oil with at least one extract solvent selected from the group consisting of C5 to C14 alkanes, chlorinated methane, chlorinated ethane, benzene, and benzene derivatives under agitation to produce a sabadilla solution, removing the solution from the de-oiled sabadilla extract, and removing the extract solvent from the solution to produce sabadilla oil.

DETAILED DESCRIPTION OF THE INVENTION

Applicant has unexpectedly developed new methods for controlling pests by applying sabadilla oil to pests or to their environment. It was unexpected that the oil from sabadilla plants would be useful as it is considered a waste product obtained during extraction of alkaloids from the plants.

Applicant did not find the presence of veratridine and cevadine in sabadilla oil, so the insecticidal qualities of the oil are not caused by known alkaloids. Accordingly, it was surprising that another part of the seed would provide insect control.

Further, Applicant unexpectedly found that sabadilla oil was much more effective than another insecticidal oil, neem oil (see for example, Example 8 below), for controlling pyrethroid-resistant bed bugs.

Applicant was unexpectedly able to develop a method for extracting sabadilla oil from *Schoenocaulon* plants that is safe, high yielding, and that produces a quality product on a commercial scale.

In a preferred embodiment, the oil is extracted from sabadilla seeds.

In one embodiment, the present invention is directed to methods for controlling pests comprising application of sabadilla oil to pests or to their environment.

In another embodiment, the pests controlled are selected from the group consisting of members of the class Insecta (insects), Arachnida subclass Acari (mites), and shell-less terrestrial gastropod mollusks (slugs).

In an embodiment, the insects controlled are selected from the group consisting of aphids (Hemiptera), whiteflies (Hemiptera), thrips (Thysanoptera), leafhoppers (Hemiptera), bed bugs (Hemiptera), psyllids (Hemiptera), scale insects (Hemiptera), mealybugs (Hemiptera), psocids (Psocoptera), lice (Phthiraptera), fleas (Siphonaptera), caterpillars (Lepidoptera), and early immature stages of beetles (Coleoptera), true bugs (Hemiptera), cockroaches (Blattodea), flies (Diptera) and wasps (Hymenoptera). In a preferred embodiment, the insects controlled are selected from the group consisting of aphids (Hemiptera), whiteflies (Hemiptera), thrips (Thysanoptera), leafhoppers (Hemiptera), bed bugs (Hemiptera), psyllids (Hemiptera), scale insects (Hemiptera), mealybugs (Hemiptera), psocids (Psocoptera), lice (Phthiraptera), and fleas (Siphonaptera). In a more preferred embodiment, the insects controlled are selected from the group consisting of bed bugs (*Cimex lectularius*), western flower thrips (*Frankliniella occidentalis*), green peach aphids (*Myzus persicae*), and greenhouse whitefly (*Trialeurodes vaporariorum*).

In a preferred embodiment, the mites controlled are two-spotted spider mites (*Tetranychus urticae*).

Sabadilla oil is a contact pesticide which means that the oil should be applied directly to the pests or their environment for the most effective control. The oil, or a formulation containing the oil, can be applied with a pressurized system, such as aerosol generators or in a form of ground application, e.g., low pressure boom sprayers, high pressure sprayers, air blast sprayers, low volume air sprayers (mist blowers), hand-operated sprayers and pump sprays. The oil should be applied as a fine spray until the surface is uniformly wet with minimal runoff. In another embodiment, the oil can be formulated, for example, as granules, and applied by broadcast.

In yet another embodiment, sabadilla oil, or a formulation containing the oil, can be applied to an absorbent material and the material can be applied in the vicinity of the area in need of treatment. For example, the oil could be placed on a piece of cloth and the cloth could be positioned in a place where bed bugs are likely to come in contact with the cloth.

In another embodiment, the present invention is directed to methods for producing an pesticidal sabadilla oil comprising milling sabadilla seeds or other plant parts, washing the milled seeds or other plant parts with at least one extract solvent selected from the group consisting of C5 to C14 alkanes, chlorinated methane, chlorinated ethane, benzene, and benzene derivatives under agitation to produce a sabadilla oil solution, removing the solution from the washed milled seeds or other plant parts, and removing the extract solvent from the solution to produce the sabadilla oil.

In another embodiment, the present invention is directed to methods for producing an pesticidal sabadilla oil comprising milling sabadilla seeds or other plant parts, washing the milled sabadilla seeds or other plant parts with at least one seed or plant part solvent selected from the group consisting of methanol, ethanol, glycol ether, ethyl lactate, propanol, butyl lactate, gamma-butyrolactone, and 1-butanol to produce a sabadilla extract solution, removing the seed and plant solvent and sabadilla extract solution from the washed milled seeds, removing the seed and plant part solvent from the solution to produce a sabadilla extract, washing the extract with at least one extract solvent selected from the group consisting of C5 to C14 alkanes, chlorinated methane, chlorinated ethane, benzene, and benzene derivatives under agitation to produce a sabadilla oil solution, removing the sabadilla oil solution from the de-oiled extract, and removing the extract solvent from the solution to produce sabadilla oil.

Sabadilla seeds and extract may be derived from any species of *Schoenocaulon*. The genus *Schoenocaulon* includes the following species: *Schoenocaulon calcicola, Schoenocaulon caricifolium, Schoenocaulon comatum, Schoenocaulon conzattii, Schoenocaulon dubium* (alt. *Schoenocaulon gracile*), *Schoenocaulon framei, Schoenocaulon ghiesbreghtii* (alt. *Schoenocaulon drummondii, Schoenocaulon yucatanense*), *Schoenocaulon ignigenum, Schoenocaulon intermedium, Schoenocaulon jaliscense, Schoenocaulon macrocarpum* (alt. *Schoenocaulon lauricola*), *Schoenocaulon madidorum, Schoenocaulon megarrhizum, Schoenocaulon mortonii, Schoenocaulon oaxacense, Schoenocaulon obtusum, Schoenocaulon officinale, Schoenocaulon pellucidum, Schoenocaulon plumosum, Schoenocaulon pringlei, Schoenocaulon rzedowskii, Schoenocaulon tenorioi, Schoenocaulon tenue, Schoenocaulon tenuifolium, Schoenocaulon texanum*, and *Schoenocaulon tigrense.*

In a preferred embodiment, the sabadilla oil can be derived from any part of the Sabadilla Lily (*Schoenocaulon officinale*) plant. In a preferred embodiment, the sabadilla oil is derived from the seeds of the Sabadilla Lily.

To optimize solvent penetration and subsequent extraction, the seed coat must be ruptured and the distance between penetrable surfaces of the seed reduced as much as possible. The can be achieved by milling the seeds.

Sabadilla seeds are very difficult to cleanly break into fine pieces. The bulk of the seed is hard and oily and requires a lot of energy to pulverize, producing heat due to high friction. Any suitable milling method can be used. Applicant found that cryogenic hammer milling the seeds was ideal for efficient extraction of the sabadilla oil.

Cryogenic grinding, or cryomilling, most commonly uses dry ice, liquid carbon dioxide or liquid nitrogen to cool the feed material in a mill of an otherwise conventional design (e.g. a cryogenic hammermill.) This super-cooling makes the sabadilla seed more uniformly brittle, in turn making it easier to control particle size. Additionally, the oil in the seed is a solid at the temperature of liquid nitrogen, and does not slow processing speed. This increased friability and solidification of the oil allows for very efficient throughput rates during milling.

Flake milling, most commonly using a roller-type mill, was found to create a milled sabadilla seed that was somewhat more efficient to handle during processing than cryogenically hammer milled seed, but allowed a less efficient extraction. In a flake milling procedure, the seeds are heated to increase plasticity and passed between rollers which flatten the seeds into thin, solvent-penetrable flakes that are still largely one piece. Flaking usually produces a minimal amount of fine particles which hinder efficient processing.

Pin milling may also be used but this technique produces particles which are coarse and require more time to process than other milling products. Conventional, ambient, hammer milling and "Fitz" milling may also be used to produce a sufficiently sized particle, however, throughput rates are generally inefficient and it is difficult to control particle size.

While flake milling's larger particle size makes it simplest and easiest to handle during processing, Applicant found that cryogenic hammer milling allowed the creation of sabadilla seed particles over a range of sizes that enable a more efficient extraction of sabadilla oil with only a modest increase in material handling difficulty. Accordingly, Applicant found that cryogenic hammer milling with liquid nitrogen was a superior milling approach for producing sabadilla oil.

The sabadilla seeds or sabadilla extract can be washed with at least one extract solvent selected from the group consisting of C5 to C14 alkanes, chlorinated methane, chlorinated ethane, benzene, and benzene derivatives one time or multiple times. For example, the sabadilla seeds can be washed one to ten times. Applicant found that more than half of the oil can be extracted from the milled seeds with a single wash. If the extract solvent is decanted and additional extract solvent added (additional washes), then the yield is increased. Applicant found that 5 washes could successfully remove 100% of the oil from the milled sabadilla seeds. For example, if 500 grams of milled seeds were washed 5 times with a total of 2.5 kilograms of hexane, 100% of the oil was removed from the milled sabadilla seeds. This is a 1:5 weight ratio of milled seed to extract solvent. This ratio can be used to scale up the production to a commercial scale. In an embodiment, the milled sabadilla seeds are washed with at least one extract solvent selected from the group consisting of C5 to C14 alkanes, chlorinated methane, chlorinated ethane, benzene, and benzene derivatives from 1 to 5 times. In a preferred embodiment, the milled sabadilla seeds are washed with the extract solvent from 2 to 5 times. In a most preferred embodiment, the milled sabadilla seeds are washed with the extract solvent 5 times.

The sabadilla extract can be washed with the extract solvent one time or multiple times. For example, the sabadilla extract can be washed one to ten times.

During the extraction, the milled sabadilla seeds and extract solvent should be agitated. This can be done by any method known by those of skill in the art. Applicant found that stirring the milled sabadilla seeds in the extract solvent increased the rate of extraction and was an effective means of agitation. The process was most efficient if the stirring was brisk enough to prevent the milled sabadilla seeds from settling in the extraction/washing vessel (e.g., flask).

During the extraction, the sabadilla extract and extract solvent should be agitated. This can be done by any method known by those of skill in the art. The process was most efficient if the stirring was brisk enough to prevent the sediment from the sabadilla extract from settling in the extraction/washing vessel (e.g., flask).

In an embodiment, the sabadilla oil solution was removed from the washed milled seeds by decanting (pouring), pumping, or draining. For example, when the extract is produced on a small scale, the milled seeds settle to the bottom of the flask and the sabadilla oil solution can be easily decanted out of the flask. During commercial extraction production, the sabadilla oil solution can be removed by methods known by those of skill in the art. For example, the sabadilla oil solution could be removed from the extraction/washing vessel by draining the sabadilla oil solution with the use of a screen, pump, or filter.

In a further embodiment, the sabadilla oil solution was removed from the de-oiled sabadilla extract by decanting (pouring), pumping, or draining. For example, when the extract is produced on a small scale, the de-oiled sabadilla extract sediment settles to the bottom of the flask and the sabadilla oil solution can be easily decanted out of the flask. During commercial extraction production, the sabadilla oil solution can be removed by methods known by those of skill in the art. For example, the sabadilla oil solution could be removed from the extraction/washing vessel by draining the sabadilla oil solution with the use of a screen, pump, or filter.

As used herein, "extract solvent" refers to C5 to C14 alkanes, chlorinated methane, chlorinated ethane, benzene, and/or benzene derivatives. As used herein, "benzene derivatives" refers to a chemical compound derived from benzene wherein one or more hydrogen atoms are replaced with another functional group. Examples of benzene derivatives include phenol, toluene, and aniline.

In a preferred embodiment, the extract solvent is hexane.

Hexane can be used at temperatures from about 0 to about 50 degrees Celsius. Applicant found that hexane at lower temperatures required additional extraction time and that temperatures above about 45 to about 50 degrees Celsius resulted in solvent loss and boiling. Applicant found that the optimal temperature for hexane extraction was from about 40 to about 45 degrees Celsius.

In an embodiment, the extract solvent is removed from the extract solvent and sabadilla oil solution by evaporation, including distillation.

The milled sabadilla seeds can be washed with at least one seed or plant part solvent selected from the group consisting of methanol, ethanol, glycol ether, ethyl lactate, propanol, butyl lactate, gamma-butyrolactone, and 1-butanol one time or multiple times. For example, the sabadilla seeds can be washed one to ten times. If the seed or plant part solvent is decanted and additional seed or plant part solvent added (additional washes), then the yield is increased.

In an embodiment, the milled sabadilla seeds are washed with the seed or plant part solvent from 1 to 5 times. In a preferred embodiment, the milled sabadilla seeds are washed with the seed or plant part solvent from 2 to 5 times. In a most preferred embodiment, the milled sabadilla seeds are washed with the seed or plant part solvent 5 times.

During the extraction, the milled sabadilla seeds and seed or plant part solvent should be agitated. This can be done by any method known by those of skill in the art. Applicant found that stirring the milled sabadilla seeds in the seed or plant part solvent increased the rate of extraction and was an effective means of agitation. The process was most efficient if the stirring was brisk enough to prevent the milled sabadilla seeds from settling in the extraction vessel (e.g., flask).

As used herein, the "seed or plant part solvent" refers to methanol, ethanol, glycol ether, ethyl lactate, propanol, butyl lactate, gamma-butyrolactone, and/or 1-butanol.

In a preferred embodiment, the seed or plant part solvent is selected from the group consisting of methanol, ethanol, glycol ether, ethyl lactate, and propanol. In a more preferred embodiment, the seed or plant part solvent is methanol.

Methanol can be used at temperatures from about 0 to about 60 degrees Celsius. Applicant found that methanol at lower temperatures required additional extraction time and that temperatures above about 55 to about 60 degrees Celsius resulted in methanol loss and boiling. Applicant found that the optimal temperature for methanol extraction was from about 50 to about 55 degrees Celsius.

In an embodiment, the sabadilla extract solution was removed from the washed milled seeds by decanting (pouring), pumping, or draining. For example, when the extract is produced on a small scale, the milled seeds settle to the bottom of the flask and the sabadilla extract solution can be easily decanted out of the flask. During commercial extraction production, the sabadilla extract solution can be removed by methods known by those of skill in the art. For example, the sabadilla extract solution could be removed from the extraction/washing vessel by draining the sabadilla extract solution with the use of a screen, pump, or filter.

In another embodiment, sabadilla oil can be extracted from milled sabadilla seeds using countercurrent extraction. Countercurrent extraction is a commercial scale extraction process typically used in oil seed extraction of seeds such as canola and soy. In brief, countercurrent extraction is a continuous process in which fresh, milled seed is fed through a long solvent bath by conveyor. The seed enters one end and the solvent enters the other, both eventually exiting opposite ends of the apparatus as spent marc (i.e. extracted/depleted seed) and miscella (i.e. solvent with a solute load from the seed).

The sabadilla oil of the present invention can also be formulated to increase the stability and/or effectiveness of the extract. The formulation could include, for example, suitable emulsifiers such as surfactants to increase the stability of the emulsion.

In an embodiment, the sabadilla oil formulation is formulated as an emulsifiable concentrate. In a preferred embodiment, the emulsifiable concentrate includes a surfactant, a solvent, and sabadilla oil.

In a preferred embodiment, the sabadilla oil is formulated to a concentration of from about 0.1 to about 8% v/v. In a more preferred embodiment, the sabadilla oil is formulated to a concentration of from about 0.5 to about 5.5% v/v. In a most preferred embodiment, the sabadilla oil is formulated to a concentration of from about 1 to about 4% v/v.

In yet another embodiment, the emulsifiable concentrate is diluted before application. In a preferred embodiment, the emulsifiable concentrate is diluted by placing from about 0.25 to about 15 ounces of the emulsifiable concentrate per gallon of water to create a homogenous emulsion for application.

In a further embodiment, the sabadilla oil formulation does not contain beta-butoxy-beta-butoxy-beta-thiocyanodiethyl-ether or kerosene.

In yet another embodiment, the methods of the present invention have an overall yield of greater than 10% sabadilla oil. In a further embodiment, the methods of the present invention have an overall yield of greater than 15% sabadilla oil. In yet a further embodiment, the methods of the present invention have an overall yield of greater than 20% sabadilla oil.

In yet another embodiment, the methods of the present invention produce a sabadilla oil that has a purity of greater than 90%. In a further embodiment, the methods of the present invention produce a sabadilla oil that has a purity of greater than 95%. In yet a further embodiment, the methods of the present invention produce a sabadilla oil that has a purity of greater than 99%.

In a further embodiment, the present invention is directed to a pesticidal sabadilla oil product produced by the process comprising the steps of milling sabadilla seeds, washing the milled sabadilla seeds with at least one extract solvent selected from the group consisting of C5 to C14 alkanes, chlorinated methane, chlorinated ethane, benzene, and benzene derivatives under agitation to produce a sabadilla oil solution, removing the sabadilla oil solution from the washed milled seeds, and removing the extract solvent from the solution to produce the sabadilla oil.

In another embodiment, the present invention is directed to a pesticidal sabadilla oil product produced by the process comprising the steps of milling sabadilla seeds, washing the milled sabadilla seeds with at least one seed or plant part solvent selected from the group consisting of methanol, ethanol, glycol ether, ethyl lactate, propanol, butyl lactate, gamma-butyrolactone, and 1-butanol to produce a sabadilla extract solution, removing the sabadilla extract solution from the washed milled seeds, removing the seed or plant part solvent from the sabadilla extract solution to produce a sabadilla seed extract, washing the sabadilla seed extract with at least one extract solvent selected from the group consisting of C5 to C14 alkanes, chlorinated methane, chlorinated ethane, benzene, and benzene derivatives under agitation to produce a sabadilla oil solution, removing the sabadilla oil solution from the de-oiled sabadilla extract, and removing the extract solvent from the sabadilla oil solution to produce the sabadilla oil.

As used herein, "sabadilla extract solution" refers to a solution containing at least one seed or plant part solvent selected from the group consisting of methanol, ethanol, glycol ether, ethyl lactate, propanol, butyl lactate, gamma-butyrolactone, and 1-butanol and the parts of the seeds which dissolve in seed or plant part solvent, such as the resins, alkaloids and oil. This solvent extraction separates the resins, alkaloids and oils from the cellulose, hemicellulose, lignin and pectin of the seeds.

As used herein, "sabadilla extract" refers to what is left after the seeds have been washed with at least one solvent selected from the group consisting of methanol, ethanol, glycol ether, ethyl lactate, propanol, butyl lactate, gamma-butyrolactone, and 1-butanol (seed or plant part extraction) and the seed or plant part solvent has been removed from extract. The lipid profile of Sabadilla oil is generally about half triglycerides, followed by diglycerides, plant waxes and monoglycerides. Free fatty acids and sterols are normally also present as minor constituents. The overall Fatty acid profile normally contains Fatty acids from C-12 to C-24, but is usually dominated by C-18, with the monounsaturated Oleic acid (C-18:1) normally the major proportion the C-18 Acids.

As used herein, "sabadilla oil solution" refers to a solution containing at least one extract solvent selected from the group consisting of C5 to C14 alkanes, chlorinated methane, chlorinated ethane, benzene, and benzene derivatives and the oils from the sabadilla seeds which dissolve in the extract solvent(s). This solvent extraction separates the oils from the rest of the extract or parts of the seeds.

As used herein, "pesticidal sabadilla oil" refers to sabadilla oil which has been separated from sabadilla seeds or other parts of the plant and is substantially free of the alkaloids veratridine and cevadine and seed material such as cellulose, hemicellulose, lignin and pectin. The sabadilla oil can contain less than 0.1% of the alkaloids veratridine and cevadine. This extract may be completely (100%) free of veratridine and cevadine.

Further, the sabadilla oil of the present invention is distinct from sabadilla oil in its natural state in the seed because the sabadilla oil has been isolated from the seed and concentrated. The sabadilla oil of the present invention is not present in nature in this form.

As used herein, "controlling pests" refers to decreasing the negative impact of pests on plants or animals to a level that is desirable to the grower or animal.

As used herein, "roller mill" refers to equipment used to decrease the shape of a material by pressing the material with at least one cylindrical roller against another roller or firm surface. A roller mill is one way of producing a flaked seed.

As used herein, "pests' environment" refers to any area that the pest is present during any life stage. One environment likely to be treated by the methods of the present invention includes the plants that the pests are living on and the surrounding soil. The pests' environment may include soil, plants, harvested plants, gardens, fields, greenhouses, or other buildings, and various indoor surfaces and structures, such as furniture including beds, and furnishings including books, clothing, etc.

As used herein, all numerical values relating to amounts, weight percentages and the like are defined as "about" or "approximately" each particular value, namely, plus or minus 10% (±10%). For example, the phrase "at least 5% by weight" is to be understood as "at least 4.5% to 5.5% by weight." Therefore, amounts within 10% of the claimed values are encompassed by the scope of the claims.

The articles "a," "an" and "the" are intended to include the plural as well as the singular, unless the context clearly indicates otherwise. For example, the methods of the present invention are directed to controlling "pests" but this can include control of a single pest (such as a single insect).

The following examples are intended to illustrate the present invention and to teach one of ordinary skill in the art how to use the extracts of the invention. They are not intended to be limiting in any way.

EXAMPLES

Example 1

Sabadilla seeds were flake milled according to the manufacturer's instructions. Two hundred grams of milled seed were added to a three liter flask with hexane at 40 to 45 degrees Celsius and stirred with a three blade stirrer controlled by an overhead motor. A stirring speed was maintained which prevented any seed fragments from settling in the flask. The system was sealed to limit evaporation loss.

The sabadilla oil solution was decanted off and additional hexane was added to the flask. This step was repeated three additional times to remove all traces of the oil from the milled seed. A total of two liters of hexane was used. The washed milled seeds remained in the bottom of the flask when the sabadilla oil solution was decanted.

The decanted sabadilla oil solution was placed in a new flask. Distillation was then used to remove the hexane from sabadilla oil solution. Standard IKA rotary evaporators were used for the distillation. The flask containing the sabadilla oil solution was loaded into the evaporator and into a heated water bath. The flask was heated to between 40 to 45 degrees Celsius in order to maximize efficient removal of the hexane without allowing it to boil over into the condenser. The evaporated hexane was condensed in an adjoining flask leaving the sabadilla oil.

Accordingly, a high purity sabadilla oil was prepared.

Example 2

The same procedure as explained in Example 1 was used except that only four total hexane washes were used. Each wash was stirred for one hour each. A high purity sabadilla oil was still obtained but this method provided a lower yield. This method, however, was the most time efficient.

Example 3

The same procedure as explained in Example 1 was used except that only three total hexane washes were used. A high purity sabadilla oil was still obtained but this method provided a lower yield than using four or five washes.

Example 4

The same procedure as explained in Example 1 was used except that only 150 grams of milled seed was used with one hexane wash. A high purity sabadilla oil was still obtained but this method provided a lower yield than using additional hexane washes.

Example 5

The same procedure as explained in Example 1 was used except that the only 150 grams of milled seed was used with one hexane wash. A high purity sabadilla oil was still obtained but this method provided a lower yield than using additional hexane washes.

Example 6

Sabadilla seeds were flake milled according to the manufacturer's instructions. Two hundred grams of milled seed were added to a three liter flask with methanol and stirred with a three blade stirrer controlled by an overhead motor. A stirring speed was maintained which prevented any seed fragments from settling in the flask. The system was sealed to limit evaporation loss.

The sabadilla extract solution was decanted off and additional methanol was added to the flask. This step was repeated three additional times. The washed milled seeds remained in the bottom of the flask when the sabadilla extract solution was decanted.

The decanted sabadilla extract solution was placed in a new flask. Distillation was then used to remove the methanol from the sabadilla extract solution. Standard IKA rotary evaporators were used for the distillation. The flask containing the sabadilla extract solution was loaded into the evaporator and into a heated water bath. The flask was heated to between 50 to 55 degrees Celsius in order to maximize efficient removal of the methanol without allowing it to boil over into the condenser. The evaporated methanol was thoroughly condensed in an adjoining flask leaving the sabadilla extract.

Accordingly, a sabadilla extract was prepared which has had the seed components, such as cellulose, removed from the milled seed. The sabadilla extract was then added to a three liter flask with hexane at 40 to 45 degrees Celsius and stirred with a three blade stirrer controlled by an overhead motor. A stirring speed was maintained which prevented any sediment from settling in the flask. The system was sealed to limit evaporation loss.

The sabadilla oil solution was decanted off and additional hexane was added to the flask. This step was repeated three additional times for all traces of the oil from the milled seed. A total of two liters of hexane was used. Sediment remained in the flask when the sabadilla oil solution was decanted off.

The sabadilla oil solution was placed in a new flask. Distillation was then used to remove the hexane from the sabadilla oil solution. Standard IKA rotary evaporators were used for the distillation. The flask containing the sabadilla oil solution was loaded into the evaporator and into a heated water bath. The flask was heated to between 40 to 45 degrees Celsius in order to maximize efficient removal of the hexane without allowing it to boil over into the condenser. The evaporated hexane was condensed in an adjoining flask leaving the sabadilla oil.

Accordingly, a high purity sabadilla oil was prepared.

Example 7

An emulsified formulation was prepared using the sabadilla oil of Example 1. The amounts of sabadilla oil, solvent and surfactant listed in Table 1 were added together and mixed until homogenous.

TABLE 1

| Emulsifiable Concentrate | | |
| --- | --- | --- |
| Component | Amount | Use |
| Sabadilla Oil | 70% | Active |
| Co-solvent | 10% | Solvent |
| Surfactant | 20% | Emulsifier |

Accordingly, Applicant prepared an easy to use product containing the sabadilla oil that is ready for immediate use or storage. The product can be diluted, for example, by the user at a rate of from about 0.25 to about 15 ounces per gallon.

Example 8

A direct spray bioassay was conducted to evaluate the efficacy of sabadilla oil against pyrethroid resistant bed bugs, Cimex lectularius. In this assay, the efficacy of sabadilla oil was compared with neem oils and imidacloprid, a neonicotinoid.

The following treatments were used in this assay:
1) Sabadilla Oil
2) Trilogy®, a 70.0% clarified hydrophobic extract of neem oil formulation (Trilogy is available from and a registered trademark of Certis USA, LLC)
3) Cirkil™ CX, a 22.0% cold pressed neem oil emulsifiable concentrate, available from Terramera, Inc.
4) Clarified hydrophobic extract of neem oil
5) A 0.05% imidacloprid formulation
6) Acetone
7) Untreated control Treatments 1 to 4 were diluted in acetone to 5.5% w/w. Treatment 5 was not diluted.

The ECL-05 strain of bugs was used in the study. This strain represents an aggregate colony of pyrethroid resistant strains of bed bugs from Minnesota, Wisconsin, Florida and New Jersey. The original stock was collected (mostly from hotel properties) by Ecolab pest management professionals in 2005. A colony of ECL-05 bed bugs is maintained by Dr. Stephen Kells' laboratory at University of Minnesota.

Colonies are maintained under standard indoor conditions of 25° C. and 14:10 (L:D) in 16 ounce glass jars with folded pieces of filter paper (Fisher 9.0 cm) for harborage and egg deposition. Jars are covered with a fine-meshed fabric (Precision Woven Nylon Mesh 193×193, McMaster Carr, Chicago, Ill., USA) with a pore size of 0.08 μm for ventilation and containment.

Colonies are fed weekly using an artificial feeding system with soon-to-expire stocks of human blood (1 unit of Type A red blood cells and 1 unit of plasma reconstituted to 600 ml of whole blood) obtained from the American Red Cross (St. Paul, Minn.).

Engorged adult bed bugs are thinned out to a 1:1 ratio of females to males to help ease the stress on the females due to the traumatic insemination and placed into a new "breeding jar" with clean filter papers. There are 50 insects to a jar (25 females, 25 males). After 7 days in the breeding jar, the filter papers containing eggs are removed and new, clean filter papers are placed into the breeding jar with the adults. These insects are then fed and eggs are collected again during the following week. Adults are used for breeding for 4 weeks before being eliminated from the colony. At any time, there are 4 to 8 breeding jars of staggered ages (0 to 4 weeks) in use in the colony.

An egg hatch occurs every 5 to 7 days. First instar nymphs are fed to repletion, which takes approximately 30 minutes in the feeding system. Weekly feeding is conducted to support the development of bed bug nymphs for 4 more weeks until the eclosion of fifth instars into adults. At the seventh week, the eclosed adults are separated by sex, some used for testing purposes, others to be placed into breeding jars to start the process over again.

Adult male bed bugs, 5 to 6 weeks old, were sorted from the colonies at the University of Minnesota using a pair of soft tissue forceps (Fisher Scientific, Pittsburgh, Pa., USA). Bed bugs were transferred to Applicant and maintained in a glass jar with a mesh screen top, as described above, in an environmental chamber (Darwin Chamber Company, Saint Louis, Mo., USA) at 27° C. and 65% relative humidity until testing.

For testing, 10 adult males were transferred into specific bed bug spray containers using soft tissue forceps. Bed bug spray containers were constructed by placing a 150 mm Whatman filter paper (Fisher Scientific, Pittsburgh, Pa., USA) onto the top of a stainless steel, round ring (10 cm in diameter and 3.25 cm in height). A second stainless steel ring of similar dimensions was then stacked on top of the base ring creating a double-ring structure with a filter paper surface in between. The sides of the double ring structure were secured with laboratory labeling tape (Fisher Scientific, Pittsburgh, Pa., USA). In the resulting setup, the filter paper provides a non-abrasive surface for bed bugs to rest on while it also serves to absorb any overspray in the container. Following the transfer of bed bugs from the colony jar, bed bugs were allowed to recover for 1 hour in the spray container before treatment application commenced.

Treatments were administered using a DeVilbiss 151 atomizer (The DeVilbiss Co., Glendale Heights, Ill., USA) attached to a Paasche D500 air compressor (Paasche Airbrush Company, Chicago, Ill., USA). Treatment volume was set at 0.50 g of treatment solution per replication. To avoid cross contamination, after each treatment, the spray apparatus was cleaned and rinsed 3 times with deionized water followed by 3 spray-through applications of dichloromethane. The cleaning procedure was completed by 3 spray-through applications of technical grade acetone.

For each treatment, the spray container system containing 10 adult male bed bugs was placed under a fume hood into a plastic shoe-box containing a secured piece of cardboard which positioned the spray container at a 45° angle. Once the spray container was in place, the sample bottle containing the appropriate treatment was shaken for 15 seconds and an aliquot of the solution was pipetted into the reservoir of the DeVilbiss atomizer. The spray apparatus was then assembled and held 5 cm from the top rim of the spray container at a 45° angle. This placement and angle ensured that the greatest area of the container was evenly exposed to the treatment. The test material was then delivered as described above. Due to bed bug availability, 6 to 11 replications were performed for each treatment.

Immediately following the spray application, bed bugs were transferred into clean 16 ounce polypropylene containers (Consolidated Plastics Co. Inc., Stow, Ohio, USA), containing 90 mm Whatman filter paper (Fisher Scientific, Pittsburgh, Pa., USA) on the bottom for recovery and observation. Ventilation holes were added to the top of the recovery containers to facilitate air exchange. Recovery containers were then transferred to the rearing chamber and maintained at 25° C. and 60% relative humidity. For the untreated control, no spray application was performed and bed bugs were transferred directly from the spray container into the recovery container for observation.

Observations of treatment response were made at 1 minute, 5 minutes, 10 minutes, 1 hour and 3 hours. Subsequent behavioral observations were made every 24 hours for 7 days.

At each assessment time, individual bed bugs were scored as:

Alive: Individual appears healthy and is able to initiate directed movement away from probing, i.e., execute normal escape behavior.

Ataxic: Individual is able to initiate directed movement away from probing but it is uncoordinated and slower than normal (either in duration and/or speed).

Knockdown: Individual is unable to engage in directional movement but appendages are vigorously moving with or without probing.

Moribund: Individual is unable to engage in directional movement but small and/or infrequent movement of appendages are detected by probing.

Dead: No response to tactile stimuli.

Affected: It is a combined category of individuals that were scored as ataxic, knockdown, moribund and dead, i.e., individuals exhibiting any signs of intoxication.

Mortality at day 7 was analyzed by one-way analysis of variance (ANOVA). Means were separated using all-pairs Tukey's honestly significant difference (HSD) test (P<0.05) (Statistix 9, Tallahassee, Fla.).

Bed bug mortality was significantly different among treatments (df=6, 52, F=84.12, P<0.00001). Results of the direct spray bioassay revealed no efficacy of various neem oil containing products against bed bugs (11 to 27% mortality, see Table 2 below). The efficacy of various neem oil containing products was not significantly different from the untreated control (P>0.05). In contrast, sabadilla oil provided 95% mortality against bed bugs. The efficacy of sabadilla oil was significantly different from all products containing neem oil (P<0.05), however, it was not significantly different from the conventional active ingredient imidacloprid (P>0.05).

TABLE 2

| | Treatment | Mortality (%)[1] |
|---|---|---|
| 1 | Sabadilla oil | 94.5 A |
| 2 | Clarified neem oil formulation | 20.0 B |
| 3 | Cold pressed neem oil | 11.7 B |
| 4 | Clarified hydrophobic extract of neem oil | 26.7 B |
| 5 | Imidacloprid | 100.0 A |
| 6 | Acetone | 16.4 B |
| 7 | Untreated Control | 8.1 B |

[1]Treatments with the same letter are not significantly different (Tukey's HSD test; P < 0.05)

Applicant unexpectedly found that sabadilla oil was highly efficacious against pyrethroid resistant bed bugs whereas neem oil based products provided no measurable efficacy against bed bugs.

Example 9

A follow-up study was conducted to assess the dose-dependent efficacy of sabadilla oil against bed bugs.

The following treatments were used in this assay:
1) Sabadilla Oil at 5.5%
2) Sabadilla Oil at 2.5%
3) Sabadilla Oil at 1.0%
4) Sabadilla Oil at 0.5%
5) Imidacloprid at 0.05%
6) Acetone
7) Untreated control The bed bugs used in this study were bred, transported, treated, and assessed as explained in Example 5 above.

Bed bug mortality was significantly different among treatments (df=6, 35, F=69.39, P<0.00001). Sabadilla oil elicited a dose-dependent efficacy response against bed bugs. This study confirmed the previously observed high efficacy of sabadilla oil diluted to 5.5% w/w against bed bugs relative to various commercial neem oil formulations (94.5% mortality in 7 days). In this study, sabadilla oil at 5.5% w/w maintained similar high efficacy against bed bugs (98.3% mortality at 7 days, see Table 3 below).

The efficacy of sabadilla oil between 1.0 and 5.5% w/w was not significantly different from the efficacy of the conventional active ingredient imidacloprid applied at 0.05% w/w at 7-days (P>0.05, Table 3). Moreover, sabadilla oil provided significantly higher mortality of bed bugs than untreated control (P<0.05) and remained highly effective against bed bugs even at 0.50% w/w concentration (70% mortality by 7 day, Table 3).

TABLE 3

| | Treatment | Mortality (%)[1] |
|---|---|---|
| 1 | Sabadilla oil at 5.5% | 98.3 A |
| 2 | Sabadilla oil at 2.5% | 91.7 AB |
| 3 | Sabadilla oil at 1.0% | 85.0 AB |
| 4 | Sabadilla oil at 0.5% | 70.0 B |
| 5 | Imidacloprid | 100.0 A |
| 6 | Acetone | 6.7 C |
| 7 | Untreated Control | 6.7 C |

[1]Treatments with the same letter are not significantly different (Tukey's HSD test; P < 0.05)

Applicant found that sabadilla oil was highly efficacious against pyrethroid resistant bed bugs at or above the threshold concentration of 0.5% w/w. These results suggest that sabadilla oil will be an effective pesticide.

Example 10

The phytotoxic potential of sabadilla oil was evaluated at i2L Research Ltd, Field Station, Shotley Bridge, UK against susceptible ornamental and vegetable plant species. Sabadilla oil was formulated as an emulsifiable concentrate per Table 1.

The test species were as follows: (1) viola (*Viola* sp.); (2) fuchsia (*Fuchsia* sp.); (3) tomato (*Lycopersicon esculentum*); (4) cucumber (*Cucumis sativus*); and lettuce (*Lactuca sativa*). Each plot comprised of 3 plants of each of the 5 varieties (15 plants per plot) with four replicates for each treatment regime. Plants were maintained in plastic pots (11 cm diameter), containing Clover™ multi-purpose, peat based compost. Treatments were carefully applied to test plants ensuring good coverage on both upper and lower leaf surfaces but avoiding run-off. Applications were made in direct sunlight and when temperatures were at 25° C. or above. An initial application was made at 0 days after treatment (or "DAA"), with a repeat application at 7 DAA. All chemicals were applied using a Cooper Pegler pressurized knapsack sprayer with hollow cone nozzle. All spray equipment was fully calibrated prior to use.

TABLE 4

| | Treatment | Rate | Application timing | Application interval |
|---|---|---|---|---|
| 1 | Water Control | N/A | 0 DAA + 7 DAA | 7 days |
| 2 | X-7578-15 | 2.0% v/v | 0 DAA + 7 DAA | 7 days |
| 3 | F-3110 | 4.0% v/v | 0 DAA + 7 DAA | 7 days |
| 4 | F-3110 | 8.0% v/v | 0 DAA + 7 DAA | 7 days |
| 5 | F-3110 | 8.0% v/v | 0 DAA + 7 DAA | 7 days |
| 6 | Sabadilla oil | 2.0% v/v | 0 DAA + 7 DAA | 7 days |
| 7 | Sabadilla oil | 4.0% v/v | 0 DAA + 7 DAA | 7 days |
| 8 | Des-X | 2.0% v/v | 0 DAA + 7 DAA | 7 days |

TABLE 5

| Plant variety | Spray volume per plot |
|---|---|
| Tomato | 25 ml |
| Lettuce | 25 ml |
| Cucumber | 50 ml |
| Viola | 25 ml |
| Fuchsia | 75 ml |
| Total/plot | 20 ml |

At 0 DAA, 1 DAA, 3 DAA, 7 DAA and 14 DAA the following information was recorded: (1) growth stage of the crop; (2) percent discoloration to foliage (describing and quantifying symptoms e.g., darker green, yellow veins, yellow areas between veins, chlorosis, whitening); (3) percent necrosis (describing and quantifying symptoms e.g., hypocotyl, tips of leaves, edges of leaves, areas between veins, burning of the "heart", total burning of leaves); (4) description and quantification of any visible deformations to whole plant, leaves or flowers (e.g., crinkling, twisting, dwarfing, curling, sticking together); (5) if flowers were present, to record and quantify any changes in terms of reduction in number of flowers, delay in bud development, delay in flowering, and discoloration. Photographic evidence was taken at each assessment in the form of: (1) pictures of entire plot; (2) picture of individual plant/plot; and (3) picture of individual leaf/plot. Crop vigor was recorded using a linear scale of 0 to 10, where 0=no crop and 10=most vigorous plot within the trial area. Climatic data was obtained throughout the entire duration of the trial and presented in the form of daily air temperature (maximum and minimum in ° C.) and relative humidity (%).

TABLE 6

| | | Injury Rating | | |
|---|---|---|---|---|
| Plant species | Variable | Sabadilla oil at 2.0% v/v (SEM) | Sabadilla oil at 4.0% v/v (SEM) | Water Control (SEM) |
| Viola | Total Phytotoxicity | 0 | 0 | 0 |
| | Discoloration | 0 | 0 | 0 |
| | Necrosis | 0 | 0 | 0 |
| | Deformation | 0 | 0 | 0 |
| | Flowering | 0 | 0 | 0 |
| | Number of flowers | 1.25 (0.16) | 1.0 (0.24) | 1.50 (0.32) |
| | Plant vigor | 10 | 10 | 10 |
| Fuchsia | Total Phytotoxicity | 0 | 1.25 | 0 |
| | Discoloration | 0 | 0 | 0 |
| | Necrosis | 0 | 0 | 0 |
| | Deformation | 0 | 1.25 | 0 |
| | Flowering | N/A | N/A | N/A |
| | Number of flowers | N/A | N/A | N/A |
| | Plant vigor | 10 | 10 | 10 |
| Tomato | Total Phytotoxicity | 0 | 0 | 0 |
| | Discoloration | 0 | 0 | 0 |
| | Necrosis | 0 | 0 | 0 |
| | Deformation | 0 | 0 | 0 |
| | Flowering | N/A | N/A | N/A |
| | Number of flowers | N/A | N/A | N/A |
| | Plant vigor | 10 | 10 | 10 |

TABLE 7

| | | Injury Rating | | |
|---|---|---|---|---|
| Plant species | Variable | Sabadilla oil at 2.0% v/v (SEM) | Sabadilla oil at 4.0% v/v (SEM) | Water Control (SEM) |
| Cucumber | Total Phytotoxicity | 0 | 0 | 0 |
| | Discoloration | 0 | 0 | 0 |
| | Necrosis | 0 | 0 | 0 |
| | Deformation | 0 | 0 | 0 |
| | Flowering | 0 | 0 | 0 |
| | Number of flowers | N/A | N/A | N/A |
| | Plant vigor | 9.83 (0.17) | 10 | 10 |
| Lettuce | Total Phytotoxicity | 0 | 0 | 0 |
| | Discoloration | 0 | 0 | 0 |
| | Necrosis | 0 | 0 | 0 |
| | Deformation | 0 | 0 | 0 |
| | Flowering | 0 | 0 | 0 |
| | Number of flowers | 0 | 0 | 0 |
| | Plant vigor | 10 | 10 | 10 |

As seen in Tables 6 and 7 above, sabadilla oil applied at 2 and 4% v/v concentration elicited no phytotoxicity response on *viola, fuchsia*, tomato, cucumber and lettuce. The emulsifiable concentrate sabadilla oil formulation was also not phytotoxic. Therefore, it was determined that sabadilla oil is suitable for agricultural and horticultural use.

Example 11

In 2016, a greenhouse screening trial was conducted at i2L Research Ltd, Field Station, Shotley Bridge, UK to evaluate the efficacy of dose dependent sabadilla oil product on potted ornamental plants (*Verbena*, variety "Homestead Purple") infested with aphids (*Myzus persicae*). Infestation levels were uniform across all plots prior to treatment application. Four (4) replications were conducted for each treatment. Each replication consisted of one plot of five ornamental plants (*Verbena*, variety "Homestead Purple"). Treatments were arranged in a randomized complete block design. All plots were contained within individually netted arenas in order to prevent migration of aphids between plots. Treatments were applied to plots using a handheld pressurized sprayer. Treatments were applied to ensure good coverage on both upper and lower leaf surfaces, but avoiding run-off. Treatment applications were made at seven day intervals with a total of 6 applications made during the course of the study. An initial pre-treatment assessment of the number of living aphids was made on Day 0, prior to treatment application. The number of aphids alive was counted on each plants weekly for 42-days. Sabadilla oil was applied at 1.0, 2.0 and 4.0% v/v, the positive control PyGanic® (PyGanic is a registered trademark of McLaughlin Gormley King Company) 5.0EC was applied at 9 fluid oz/acre and the untreated control only received water equivalent of the total volume of the treatment solution.

Treatment efficacy was determined by comparing the cumulative number of aphids recorded over the 42-day duration of the study. Data was subjected to analysis of variance for randomized complete block design and means were separated by Tukey's HSD test (P<0.05). Tukey, John, "Comparing Individual Means in the Analysis of Variance". *Biometrics* 5 (2): 99-114. The results of this study can be seen below in Table 8.

TABLE 8

Dose-dependent efficacy of sabadilla oil against soft bodied arthropods (green peach aphids)

| Treatment | Concentration or rate | Mean number of green peach aphids at Time 0 | Cumulative mean number of green peach aphids over 42-days[1] |
|---|---|---|---|
| Sabadilla oil | 1.0% v/v | 75.5 a | 1716.0 b |
|  | 2.0% v/v | 73.8 a | 999.8 bc |
|  | 4.0% v/v | 73.0 a | 490.3 c |
| PyGanic ® 5.0EC | 9 fl.oz/acre | 72.3 a | 1121.5 bc |
| Untreated (water only) | N/A | 72.3 a | 5511.5 a |

[1]Values with different letters are significantly different (Tukey's HSD test P < 0.05).

Results demonstrate a dose dependent effectiveness of sabadilla oils of the present invention against green peach aphids.

Example 12

In 2016, a greenhouse screening trial was conducted at i2L Research Ltd, Field Station, Shotley Bridge, UK to evaluate the efficacy of dose dependent sabadilla oil product on potted tomato infested with two spotted spider mites (*Tetranychus urticae*). Infestation levels were uniform across all plots prior to treatment application. Four (4) replications were conducted for each treatment. Each replication consisted of one plot of five tomato plants. Treatments were arranged in a randomized complete block design. All plots were contained within individually netted arenas in order to prevent migration of spider mites between plots. Treatments were applied to plots using a handheld pressurized sprayer. Treatments were applied to ensure good coverage on both upper and lower leaf surfaces, but avoiding run-off. Treatment applications were made at seven day intervals with a total of 6 applications made during the course of the study. An initial pre-treatment assessment of the number of living spider mites was made on Day 0, prior to treatment application. The number of spider mites alive was counted on each plants weekly for 42-days. Sabadilla oil was applied at 1.0, 2.0 and 4.0% v/v, the positive control PyGanic® 5.0EC was applied at 9 fluid oz/acre and the untreated control only received water equivalent of the total volume of the treatment solution.

Treatment efficacy was determined by comparing the cumulative number of spider mites recorded over the 42-day duration of the study. Data was subjected to analysis of variance for randomized complete block design and means were separated by Tukey's HSD test (P<0.05). The results of this study can be seen below in Table 9.

TABLE 9

Dose-dependent efficacy of sabadilla oil against soft bodied arthropods (twospotted spider mites)

| Treatment | Concentration or rate | Mean number of twospotted spider mites at Time 0 | Cumulative mean number of twospotted spidermites over 42-days[1] |
|---|---|---|---|
| Sabadilla oil | 1.0% v/v | 61.0 a | 146.8 b |
|  | 2.0% v/v | 53.0 a | 128.5 b |
|  | 4.0% v/v | 66.5 a | 155.5 b |
| PyGanic ® 5.0EC | 9 fl.oz/acre | 60.0 a | 423.5 b |
| Untreated (water only) | N/A | 63.0 a | 2393.3 a |

[1]Values with different letters are significantly different (Tukey's HSD test P < 0.05)

Results demonstrate a dose dependent effectiveness of sabadilla oils of the present invention against two spotted spider mites.

Overall these studies demonstrate the efficacy of sabadilla oil against soft bodied arthropods, such as aphids, thrips, whiteflies, and mites using green peach aphids and two spotted spider mites as model species.

We claim:

1. A method for producing a pesticidal sabadilla oil consisting essentially of milling sabadilla seeds; washing the milled sabadilla seeds with butyl lactate under agitation to produce a sabadilla oil solution; distilling the solution; and removing the extract solvent from the solution to produce the sabadilla oil.

* * * * *